US009433436B2

(12) United States Patent
Schon et al.

(10) Patent No.: US 9,433,436 B2
(45) Date of Patent: *Sep. 6, 2016

(54) THERAPEUTIC MATERIAL DELIVERY SYSTEM FOR TISSUE VOIDS AND CANNULATED IMPLANTS

(71) Applicant: BIOACTIVE SURGICAL, INC., Clarksville, MD (US)

(72) Inventors: Lew C. Schon, Baltimore, MD (US); Richard H. Spedden, Clarksville, MD (US); Laura J. Pingel, Ellicott City, MD (US)

(73) Assignee: Bioactive Surgical Inc., Clarksville, MD (US)

( * ) Notice: Subject to any disclaimer, the term of this patent is extended or adjusted under 35 U.S.C. 154(b) by 503 days.

This patent is subject to a terminal disclaimer.

(21) Appl. No.: 13/935,819

(22) Filed: Jul. 5, 2013

(65) Prior Publication Data

US 2013/0296828 A1 Nov. 7, 2013

Related U.S. Application Data

(63) Continuation-in-part of application No. 13/588,110, filed on Aug. 17, 2012, now abandoned, which is a continuation-in-part of application No. 12/414,194, filed on Mar. 30, 2009, now Pat. No. 8,317,799.

(60) Provisional application No. 61/116,465, filed on Nov. 20, 2008, provisional application No. 61/154,718, filed on Feb. 23, 2009.

(51) Int. Cl.
| | |
|---|---|
| *A61B 17/58* | (2006.01) |
| *A61B 17/60* | (2006.01) |
| *A61F 2/00* | (2006.01) |
| *A61B 17/34* | (2006.01) |

(Continued)

(52) U.S. Cl.
CPC ....... *A61B 17/3472* (2013.01); *A61B 17/3468* (2013.01); *A61F 2/28* (2013.01); *A61M 5/3295* (2013.01); *A61B 17/3478* (2013.01); *A61B 17/864* (2013.01); *A61M 31/00* (2013.01)

(58) Field of Classification Search
CPC .......... A61B 17/8802; A61B 17/8805; A61B 17/8088; A61B 17/8011; A61B 17/8819; A61B 17/8822; A61B 17/8825; A61B 17/8827; A61B 17/8833; A61F 2/4601; A61F 2/4614; A61F 2/30723; A61F 2/3472
USPC ...................................................... 606/92–94
See application file for complete search history.

(56) References Cited

U.S. PATENT DOCUMENTS

| | | |
|---|---|---|
| 5,681,289 A | 10/1997 | Wilcox et al. |
| 5,868,697 A | 2/1999 | Richter et al. |

(Continued)

*Primary Examiner* — Kevin T Truong
*Assistant Examiner* — Si Ming Ku
(74) *Attorney, Agent, or Firm* — Chalin A. Smith; Smith Patent, LLC

(57) ABSTRACT

Described herein is a novel drug delivery assembly having particular applicability to the field of orthopedic and surgical medicine. The devices and assemblies described herein enable the efficient application and retention of potentially expensive therapeutic materials to very specific locations, particularly those associated with voids in bone and tissue. One particularly unique aspect of the present invention involves the introduction of constructs which promote the retention of therapeutic material in the target area of application for beneficial use, for example by forming a proximal barrier that prevents leakage of the therapeutic material out of the target area. Additionally, the present invention provides unique devices and methods for surgical introduction of such constructs. The present invention finds particular application in connection with introduction of stem and progenitor cells, bioactive molecules and bone scaffold materials in conjunction with bone voids and with the use of cannulated implants, such as bone screws (also surgical screws) and pins. The present invention also has beneficial use in the delivery of cancer drugs, antimicrobials, bone cements and other therapeutic materials.

18 Claims, 3 Drawing Sheets

(51) Int. Cl.
  *A61F 2/28* (2006.01)
  *A61M 5/32* (2006.01)
  *A61B 17/86* (2006.01)
  *A61M 31/00* (2006.01)

(56) References Cited

U.S. PATENT DOCUMENTS

| | | |
|---|---|---|
| 5,871,484 A | 2/1999 | Spievack et al. |
| 6,019,761 A | 2/2000 | Gustilo |
| 6,210,376 B1 | 4/2001 | Grayson |
| 6,530,896 B1 | 3/2003 | Elliott |
| 7,235,107 B2 | 6/2007 | Evans et al. |
| 7,354,442 B2 | 4/2008 | Sasso et al. |
| 2005/0015061 A1 | 1/2005 | Sweeney |
| 2006/0184246 A1 | 8/2006 | Zwirkoski |
| 2006/0241593 A1 | 10/2006 | Sherman et al. |
| 2006/0246103 A1 | 11/2006 | Ralph et al. |
| 2007/0010827 A1 | 1/2007 | Tu et al. |
| 2007/0162024 A1 | 7/2007 | Siemonsmeier |
| 2008/0033572 A1 | 2/2008 | D/Antonio et al. |

THERAPEUTIC MATERIAL DELIVERY SYSTEM FOR TISSUE VOIDS AND CANNULATED IMPLANTS

PRIORITY

This application is a continuation-in-part of U.S. patent application Ser. No. 13/588,110 filed Aug. 17, 2012, which, in turn, is a continuation-in-part of U.S. patent application Ser. No. 12/414,194, filed Mar. 30, 2009, now U.S. Pat. No. 8,317,799, which, in turn, claims priority to U.S. Provisional Application Ser. No. 61/116,465, filed Nov. 20, 2008 and U.S. Provisional Application Ser. No. 61/154,718, filed Feb. 23, 2009, all of which are hereby incorporated by reference in their entirety.

FIELD OF THE INVENTION

The present invention relates to drug delivery, particularly in the field of orthopedic and surgical medicine. More particularly, the invention relates to devices and assemblies that enable the efficient application and retention of potentially expensive therapeutic materials to very specific locations, particularly those associated with voids in bone and tissue.

One particularly unique aspect of the present invention involves the introduction of constructs which promote the retention of therapeutic material in the target area of application for beneficial use, for example by forming a proximal barrier that prevents leakage of the therapeutic material out of the target area. Additionally, the present invention provides unique devices and methods for surgical introduction of such constructs.

The present invention finds particular application in connection with introduction of stem and progenitor cells, bioactive molecules and sealing, barrier and scaffold materials in conjunction with bone voids and with the use of cannulated implants, such as bone screws (also surgical screws) and pins. The present invention also has beneficial use in the delivery of cancer drugs, antimicrobials, bone cements and other therapeutic materials.

BACKGROUND OF THE INVENTION

Many orthopedic surgical procedures require the introduction of therapeutic, remedial or other beneficial material into or through holes created in the bone as part of the surgical process, whether by drilling, use of a coring device, use of a self-drilling screw or use of other mechanism. Bone or cartilage penetrations may be formed through the use of trocars and drills as a point of entry for many surgical procedures, including the introduction of liquid or paste type therapeutics and cements. In this context, cannulated screws and pins are used extensively to join tissues to bone and cartilage or connect sections of bone and/or cartilage. In many cases where holes are formed in bone, there is an advantage in providing a plug or seal in the hole or implanted cannulated device to assure retention of the therapeutic material in the desired area of effect.

Growth factors, bioactive molecules, stem and progenitor cells and other therapeutically beneficial material introduced into a damaged or diseased bone or at a bone-tissue junction through natural, disease-associated, or surgically induced holes or through cannulated implants can speed the healing process and/or address an underlying osteopathology (such as bone disease or bone cancer). Bone cements and other remedial materials can also be introduced through such natural or surgical penetrations, for example to correct a non-union deficiency or to fill voids created by failure of bone structure following previous surgery. Often antibiotics are introduced to correct or prevent infection. Chemotherapy agents can also be introduced to combat cancerous growth. Chemicals to permit detection of voids using conventional radiographic or other techniques also can be introduced through surgical holes or cannulated implants.

Problematic issues associated with the accurate and efficient placement of such therapeutic, remedial or other beneficial material at a specific points in a surgical penetration, such as one bridging the juncture of two bone sections, include, for example:

1. In those cases where the therapeutic material is injected through a hypodermic needle, difficulty can arise from the fact that confirmation of the needle tip location relative the juncture point is not easily available. In the case of minimally invasive techniques, the depth of soft tissue over the bone varies between patients and body areas and can actually fluctuate during surgery because of soft tissue swelling. Consequently, the depth of needle penetration in the bone itself may not be readily apparent, and use of radiological or other imaging means to confirm placement requires expensive equipment and is time consuming. Further, needle penetration into a bone screw or other device that is opaque to imaging technologies must be inferred rather that directly observed, which introduces an element of potential error.
2. Injected therapeutic material tends to rapidly flow out of the desired zone of application, particularly in the proximal direction (away from the target site), most often though the very hole created in the bone for the surgical procedure.
3. The therapeutic material may need to be introduced under pressure to successfully penetrate the surrounding tissue of interest, and an open hole does not support this pressurization.

Cannulated surgical screws are conventional in surgical procedures, particularly in the context of orthopedic surgery. The current state of the art provides for the injection of therapeutic materials into the bore of said screws, such that said material can potentially migrate to the distal end or tip of the screw and into the tissue there for therapeutic effect. In addition, fenestrated screws, provided with generally laterally disposed pores or "fenestrations", have been proposed to permit material introduction in areas around the screw threads or at the discontinuity of tissue, usually bone sections, being joined. However, since cannulated screws are open at both ends, there is the potential for the expensive therapeutic material being introduced to flow out either end of the screw, rather than through the fenestrations, as desired.

To address the issue of leakage, specially designed screws with integral valves have been proposed to prevent flow out of the proximal end or "head" of a bone screw; however, these type devices have the disadvantages of being overly specialized for a particular application. In addition, they are in many cases not compatible with the standard hex head driver tools available in many operating rooms. Caps, which can be placed on the head of a screw, have also been proposed. However, these also interfere with the driving of the screw or need to be installed after the screw is in place, potentially requiring unobstructed access to the screw head, which is not always possible. Additionally, cannulated surgical screws are often directed to the point of application by sliding the screw over a guidewire that has been inserted in or through the bone. The guidewire makes the pre-placement of a flow restriction in a screw prior to screw placement problematic.

Thus, there remains a need in the art, particularly in the case of cannulated surgical screws, for a generally applicable device and method that provides for efficient and restricted delivery and retention of therapeutic materials to a target location associated with a tissue void, preferably one that is readily adaptable for use with other surgical and interventional instruments that standard and conventional in the art.

SUMMARY OF THE INVENTION

In view of the aforementioned need in the art, the present invention provides devices and assemblies uniquely characterized for the delivery and retention of therapeutic material into bone, cartilage and similar tissues or through those tissues into other tissue. The novelty of the present invention is based not only its unique configurations, but also on the interaction between its parts, where each component provides multiple functions that combine to provide a functionality not available in current art.

In Applicants' prior patent application, U.S. Ser. No. 12/414,194, Applicants describe advantages and methods for a device where a deformable plug is pushed through a "plug guide" into a void. The present invention relates to the use of flowable plugs and the methods of introducing such plugs through cannulas or ports so as to form a plug in place in the bone screw or void. Central to the instant invention is the provision of a flowable material (also "caulking") suited for injection through a cannula or port into a tissue or implant device, such as a bone screw, such that once implanted the flowable material forms a plug capable of impeding flow of the therapeutic material in the proximal direction. In this manner, the plug of the present invention promotes the retention of the beneficial material injected on the distal side of the plug and in the region of desired effect. In addition to serving as a proximal barrier to flow, the plug of the present invention can also itself act as a means for delivering therapeutic, remedial or other beneficial material. For example, therapeutic materials included in the plug material may diffuse over time into adjacent areas and tissues. These beneficial therapeutic materials, may include, but not be limited to materials such as growth factors, stem cells, antibiotics and the like. Particulars regarding the preferred materials for the flowable plug construction as well as the preferred therapeutic materials are discussed in greater detail below.

In one embodiment of the present invention, the device comprises an "adapter section" as a main body, with a proximal and a distal end and two or more material delivery cannulas transversing the adapter section from the proximal end to the distal end. Additionally, where in at least one of the fluid delivery cannulas, the primary therapeutics delivery cannula (the "therapeutics needle") comprises a hypodermic needle or similar fluid delivery cannula which can be moved along the linear axis independently of the adapter section and wherein in one state the distal end extends beyond the distal end of the adapter section to a distance wherein a flowable plug material can be introduced between the distal end of the adapter section and the distal end of the therapeutics needle without impeding flow out of the therapeutics needle.

The distal end of the adapter section is configured to mate with the proximal opening (head) of a bone screw or the surface opening of a void in tissue (such as a drill hole in bone). Numerous configurations can be envisioned for the distal end of the adapter section, including but not limited to: a tapered section which permits the adapter section to fit a variety of hole sizes, an enlarged face section to mate against a flat face, a shaped section to match a cross-sectional shape such as the hex drive pattern in a bone screw, and a deformable distal end such that the adapter section can conform to a variety of opening shapes or even an irregular opening shape.

In one method of the present invention, the distal end of the adapter section is placed in contact with the proximal end of the bone screw or void. Through this positioning, the therapeutics needle is also established in the desired position extending through the adapter section and projecting from the distal end of the device into the bone screw by a predetermined distance. Alternately the needle may be introduced into that configuration once the adapter section is in place. The flowable plug or caulking material is then injected into the bone screw or tissue void and into the space between the distal end of the adapter section and the distal end of the therapeutics needle. Once the caulking material is in place, the primary therapeutic is injected into the void at the distal side of the plug. In the preferred embodiment, the therapeutics needle is then retracted while the adapter section is held in place to assist in retaining the caulking material in the void, and then the adapter section is removed. However, still consistent with the present invention the therapeutics needle and adapter section may be removed simultaneously in cases where the caulking material is found to remain in the void during such a process.

In another aspect of the present invention, the distal face of the adapter section can be treated with material to reduce the potential for undesired binding of the caulking material to the face of the adapter section. Examples of such treatment include use of materials such as Polytetrafluoroethylene (PTFE), known for low surface binding, or the application of lubricants such as silicone lubricants.

In a second embodiment of the present invention, the flowable plug material is retained within a reservoir internal to the device and the relative motion along the lineal axis of the device of the portion of the device linked with the therapeutic injection needle and the portion of the device housing the plug material and in direct contact with the bone screw or patient tissue results in displacement of the flowable plug material through a port in the device and into the void of the bone screw or tissue to form the desired plug. As with the first embodiment, the therapeutic material can then be injected into the void on the distal side of the plug, and the therapeutics needle can be retracted while the rest of the device holds the plug in place in the bone screw or tissue.

In addition to the devices described, the described methods of use are also aspects of the present invention.

These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

Examples, drawings and descriptions, herein, may refer to specific tissue and/or implant device constructs where the device might be applied, such as cannulated bone screws; however, the devices, assemblies, and methods of the present invention are equally applicable to other situations, for use with any other medical implant devices having a fluid port or hollow core, as well as to holes in tissue, including those which are surgically induced or the result of defect disease or trauma. Additionally, examples, drawings and descriptions typically refer to human patients; however the constructs of this invention are equally applicable to other biological entities.

BRIEF DESCRIPTION OF THE DRAWINGS

Various aspects and applications of the present invention will become apparent to the skilled artisan upon consideration of the brief description of the figures and the detailed description of the present invention and its preferred embodiments that follows.

FIG. 1 depicts the components of the present invention as individual elements and as an assembled device as may be provided in a sterile package for use in surgery. The individual elements can vary in design as might be envisioned by one skilled in the art without modifying the purpose of the elements or the interaction between elements, which is fundamental in the present invention. The elements of FIG. 1 include:

Hypodermic needle or other therapeutic material flow tube (also Therapeutics Needle) (1)
   Main Body and Adapter Section (2)
   Flowable Plug Delivery Cannula (3)
   Sharps Protection Sleeve (Optional) (4)

Figure 1:
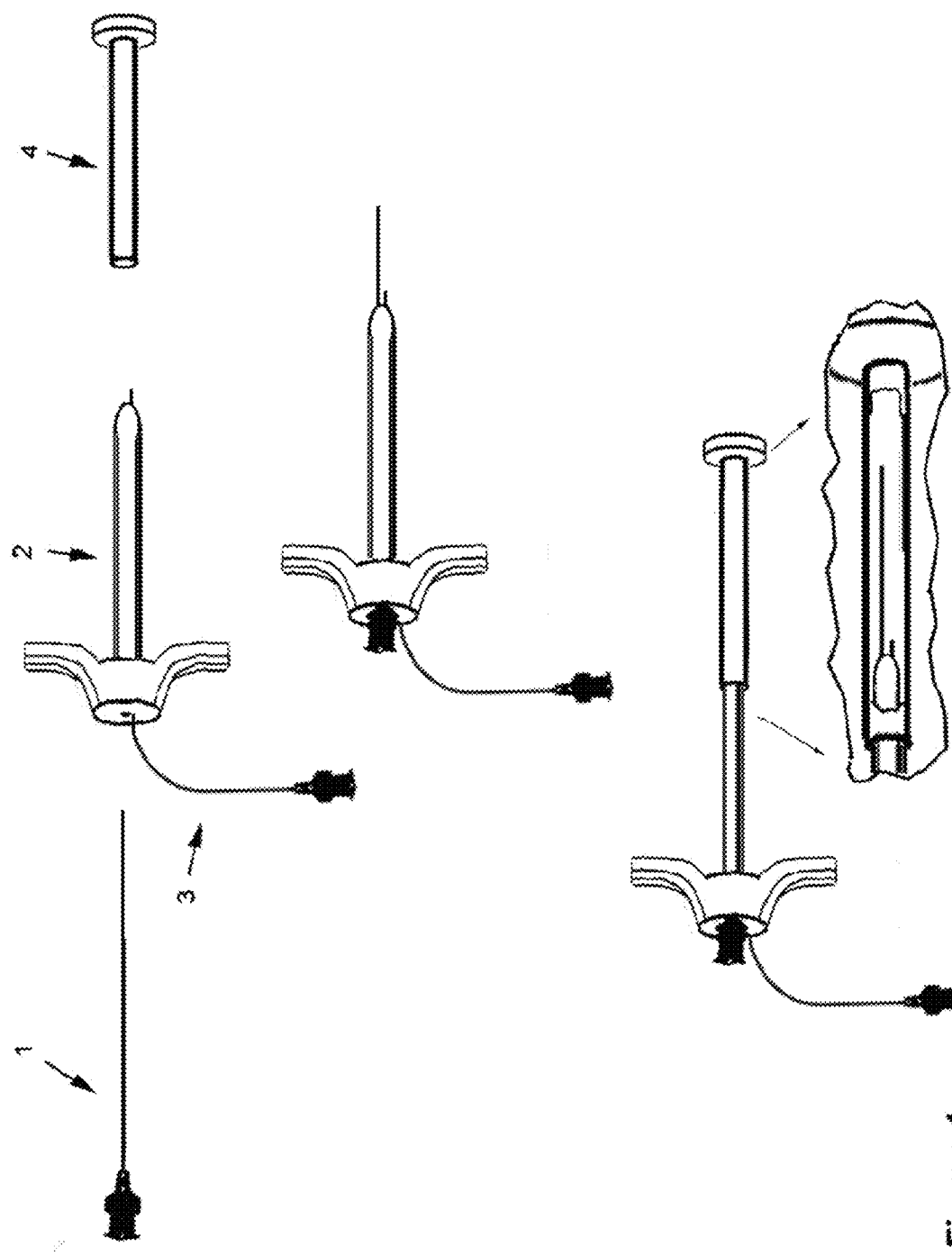
FIGS. 1 and 2 depict one embodiment of the present invention.

The cut-away view in FIG. 1 depicts the positioning of the optional Sleeve (4) in a manner where the device can be handled without the sharp points of the needles or cannulas (1 and 3) being exposed during surgery prior to insertion. It is a novel aspect of the present invention that the distal end of the Sleeve (4) can be placed against the proximal end of the bone screen or void, and that the motion of pushing the Adapter (2) towards the bone screw or void results in the distal end of the Adapter (2) and the sharps (distal ends of 1 and 3) being displaced through the Sleeve and against or into (respectively) the bone screw or void.

Figure 2:
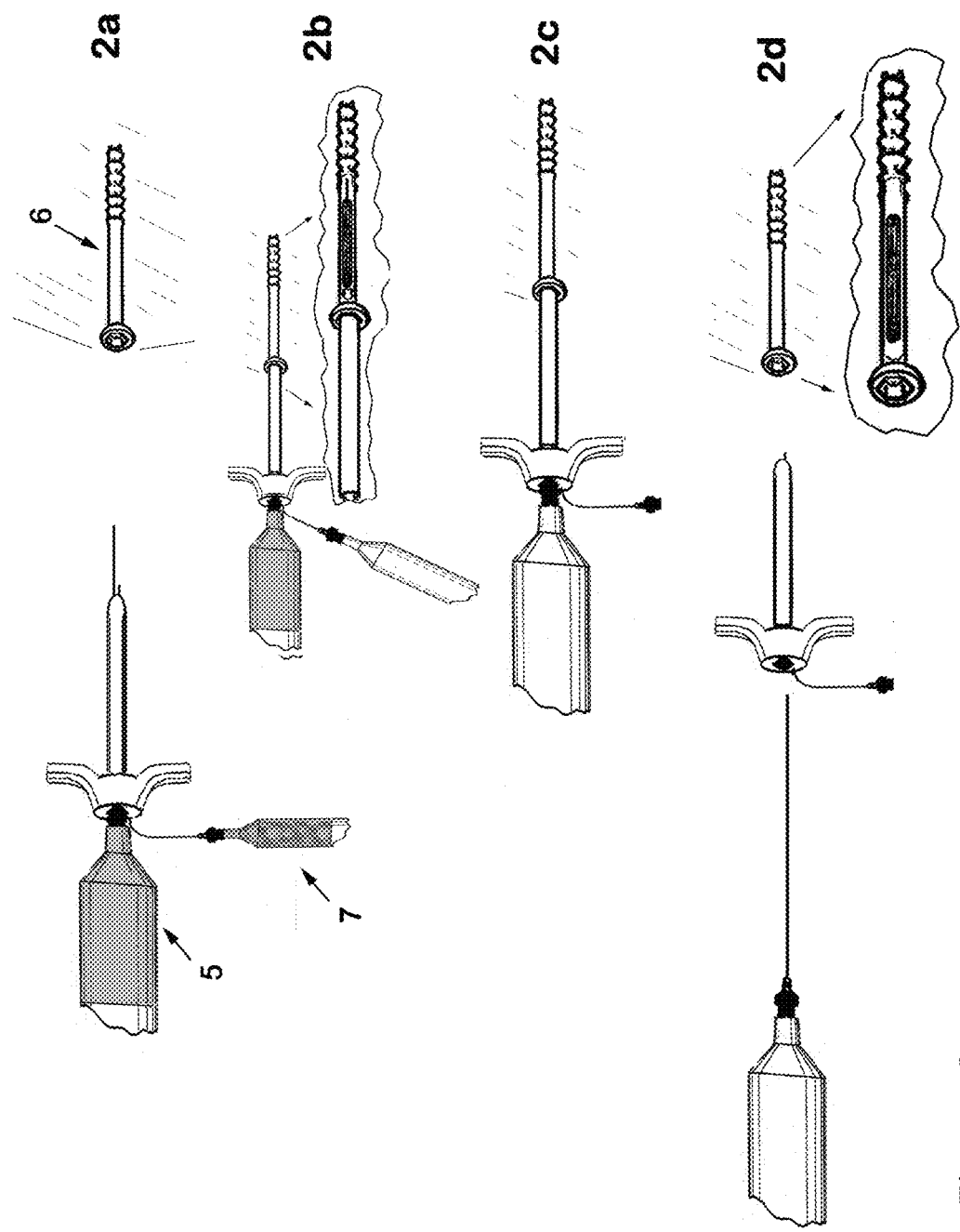

FIG. 2 depicts the sequence of use of the device. In Frame 2*a*, a syringe or reservoir (5) with therapeutic liquid is attached to the hypodermic or therapeutics needle of the device using a conventional luer-lock-type fitting, though other common attachment mechanisms are also contemplated. A flowable plug material reservoir and dispensing mechanism (7) is attached to a fluid flow cannula (or hypodermic needle) using a conventional luer-lock-type fitting, though other common attachment mechanisms are also contemplated. In this example, the target destination for the therapeutic fluid is the bore of a bone screw (6) embedded in bone. In Frame 2*b*, the distal end of the adapter is inserted into the hex driver fitting in the proximal end of the bone screw. In the example tapered end of the adapter allows the adapter to mate to the perimeter of the bore of the bone screw. Also in this frame, the flowable plug material has been injected into the bore of the bone screw. Frame 2*c* depicts the position of all elements after the therapeutic material has been injected into the bone screw. In the preferred embodiment, the therapeutic material delivery needle is then removed while the adapter is held in place. Removal of the therapeutics needle with the adapter held in place reduces the potential for flowable plug material to adhere to the therapeutics needle and be drawn out of the bone screw when the needle is removed. Frame 2*d* depicts the plug remaining in the bone screw after the adapter and the syringe/hypodermic needle assemblies have been removed.

Figure 3:
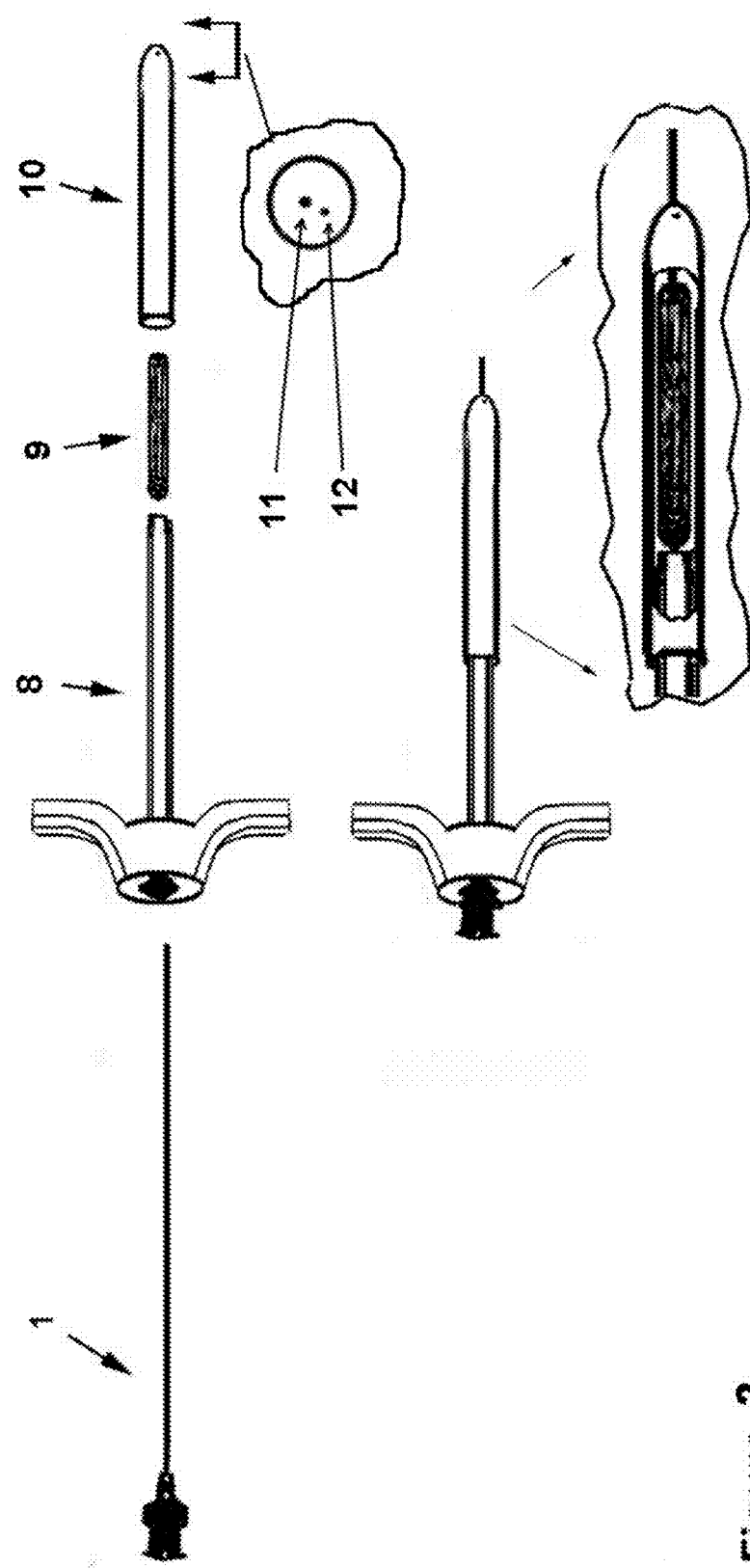

FIG. 3 depicts a second embodiment of the present invention. This embodiment is similar to embodiments disclosed by Applicants' in parent application Ser. No. 12/414,194, the contents of which are incorporated by reference herein. The unique aspect of this embodiment is the use of the flowable plug material (9) discharged through a constrained port such that the plug flows into and fills the cross-section of the void through flow rather than expansion. FIG. 3 depicts the components of the present invention as individual elements and as an assembled device as may be provided in a sterile package for use in surgery. The individual elements can vary in design as might be envisioned by one skilled in the art without modifying the purpose of the elements or the interaction between elements which is fundamental in the present invention. The elements of FIG. 3 include:

Hypodermic needle or therapeutic material flow tube—Therapeutics Needle (1)
Main Body, Plug Pusher and Needle Guide (8)
Flowable Plug Material (9)
Plug Guide Cannula and Adapter Section (10)
Penetration in Plug Guide Cannula Distal End for Therapeutics needle (11)
Port in Plug Guide Cannula Distal End for discharge of flowable plug material into the target bone screw or void (11)

The Port 11 can be located in any orientation on the distal end of the Adapter section (10) appropriate to allow delivery of the flowable plug material into the target screw or void once the adapter is placed against the screw or void. Port 11 can also be in the form of a concentric opening around or in common with Penetration (11). Port 11 can be one or more openings in the distal end of the Adapter section.

The cut-away view in FIG. 3 depicts the positioning of the flowable plug material in the Plug Guide Cannula and Adapter Section (10). This arrangement provides for several clear advantages:

a. The flowable plug material can be preloaded and constrained in this enclosed area. A removable protective cap (not depicted, but another aspect of the present invention) covering the distal end of the Adapter Section can seal the ports (12) and further contain the flowable plug material as well as protect it from air and contaminants prior to use. That same or a different protective cap can also provide sharps protection for the hypodermic needle.

b. The Plug Guide Cannula can include multiple zones and even a mixing zone for the use of two or more part cement systems, such as a 2-part epoxy.

c. The properties of the flowable plug material can be varied along the linear axis of the cannula and since discharge from the cannula is from the distal end only, a certain degree of plug property variance along the linear axis of the implant plug can be achieved.

DETAILED DESCRIPTION OF THE PREFERRED EMBODIMENTS

The present constitutes a marked improvement in the area of injection of therapeutic materials into voids in tissue such as bone and/or implant devices such as bone screws, not only because it provides multiple functions in a single device, which both saves time and reduces the potential for error during surgery, but also because the interaction between the parts provides functionality not available if the components were implanted individually. Noted advantages include:

- The flowable plug material allows the device to form a wide range of plug diameters where a single device can be utilized with a variety of bone screw sizes.
- The flowable plug material is maintained and constrained in a protective enclosure prior to use, either a separate dispensing device such as a caulking gun or hypodermic type device or in one embodiment the Plug Guide Cannula.
- The therapeutics needle transits the length of the plug prior to and during insertion in the body tissue (or implanted device). As the plug is formed in the bone screw, the distal tip (discharge end) of the therapeutics needle is either already extended to into the bone screw or is advancing into the bone screw as the plug is formed.
- The device provides a positive means to set both the plug depth and the needle tip depth in the tissue.
- The plug pusher holds the plug in place during the injection of therapeutic material, thereby allowing the surgeon to apply a force sufficient to overcome hydraulic resistance in the surrounding tissue, not only assuring delivery of the therapeutic, but also providing important tactile feedback to the surgeon. If the surgeon were just to inject through a plug, there is the potential for the plug to 'blow back'.
- The plug pusher can hold the plug in place while the needle is being extracted; otherwise friction between the needle and the plug might pull the plug part or all of the way out of the hole in the bone or bore of the screw.

Elements of the Present Invention:

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which the present invention belongs. However, in case of conflict, the present specification, including definitions, will control.

In the context of the present invention, the following definitions apply:

The words "a", "an" and "the" as used herein mean "at least one" unless otherwise specifically indicated. Thus, for example, reference to a "molecule" is a reference to one or more molecules and equivalents thereof known to those skilled in the art, and so forth.

The term "proximal" as used herein refers to that end or portion which is situated closest to the user of the device, farthest away from the target surgical site.

The term "distal" as used herein refers to that end or portion situated farthest away from the user of the device, closest to the target surgical site.

The term "axial" as used herein refers to the direction relating to or parallel with the longitudinal axis of the device. In the context of the present invention, the plug positioned within the bore of the plug guide cannula and may be axially (distally) moved therein and displaced therefrom by means of a plug pusher or plunger.

The term "lateral" as used herein refers to the direction relating to the transverse axis of the device. In the context of the present invention, the target site may be provided with a fenestrated surgical screw having a series of pores or fenestrations positioned about its lateral surface.

The present invention is directed, at least in part, to the introduction and retention of therapeutic materials (also referred to herein as remedial, beneficial and/or therapeutic agents) through holes or voids in bodily tissue or through the bore of an implanted device. In the context of the present invention, the term "therapeutic", "therapeutic materials" and "remedial", "beneficial" and "therapeutic" "agents" refers to any material which is, or can be, injected through a hypodermic needle or other cannula device, into tissue with an intended effect which is advantageous to the health or well-being of the patient. Of particular value in the context of the present invention are those agents with known benefit to the musculoskeletal system, such as, stem and precursor cells and other biological cells, bioactive cytokines (particularly growth factors, bone morphogenetic protein, angiogenesis factors), hormones, adipose extracts, anti-cancer drugs (including chemo-therapy agents), bone cements and mixtures comprising in part calcium bearing molecules, antibiotics and other anti-infection agents, blood thinning agents, analgesics, DNA and combinations of any or all of the above. In the context of the present invention, bone marrow aspirate and compositions comprising such are of particular value.

In the context of the present invention, the term "stem cell" represents a generic group of undifferentiated cells that possess the capacity for self-renewal while retaining varying potentials to form differentiated cells and tissues. Stem cells can be totipotent, pluripotent or multipotent. Derivative stem cells that have lost the ability to differentiate also occur and are termed 'nullipotent' stem cells. A totipotent stem cell is a cell that has the ability to form all the cells and tissues that are found in an intact organism, including the extra-embryonic tissues (i.e. the placenta). Totipotent cells comprise the very early embryo (8 cells) and have the ability to form an intact organism. A pluripotent stem cell is a cell that has the ability to form all tissues found in an intact organism although the pluripotent stem cell cannot form an intact organism. A multipotent cell has a restricted ability to form differentiated cells and tissues. Typically adult stem cells are multipotent stem cells and are the precursor stem cells or lineage restricted stem cells that have the ability to form some cells or tissues and replenish senescing or damaged cells/tissues. Further information may be found in WO 08/007,082, the contents of which are incorporated by reference herein.

In the context of the present invention, the term "progenitor cell" refers to unipotent or multipotent cells, which comprise the stage of cell differentiation between stem cells and fully differentiated cells.

In the context of the present invention, the term "biological cell" refers to any cell capable of performing useful biological functions in a living organism, particularly replication to form a tissue structure. The term as used herein includes stem cells, progenitor cells and fully differentiated cells. Biological cells may include cells from the intended host organism or those from a donor organism. Biological cells can include cells from recombinant or genetic engineering techniques.

In the context of the present invention, the term "bioactive molecules" refers to any molecule which has the capacity to interact with a living tissue or system in such a way as to exhibit or induce a biological activity in an organism, tissue, organ or cell, either in vivo, in vitro or ex vivo. The term "bioactive molecule" extends to precursor forms thereof. Precursor proteins, for example BMP precursors, are typically inactive until they undergo endoproteolytic cleavage; however, in that this is a process that naturally occurs in the body, the present invention extends to precursor proteins that participate in useful biological processes in the body.

The term "therapeutic agents" as used herein refers to any molecule, compound or composition having therapeutic potential, more particularly pharmaceutical activity. Examples of particularly useful therapeutic and/or pharmaceutical activities include but are not limited to anti-coagulation activity, anti-adhesive activity, anti-microbial activity, anti-proliferative activity, and biomimetic activity.

In the context of the present invention, the term "therapeutic materials" refers to any composition which comprises any of the following: therapeutic agents, bioactive molecules, stem cells, progenitor cells or biological cells. The term "bioactive solution" refers to a liquid composition which comprises, in part, bioactive materials.

In the context of the present invention, the term "antimicrobial" refers to any molecule which has the capacity to limit or interfere with the biological function of a bacterial, fungal or viral pathogen or a toxin. Antimicrobial is intended to also encompass antibacterial, antibiotics, antiseptics, disinfectants and combinations thereof.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue, and additional specialized tissue, such as teeth. These tissues make up all the organs, structures and other body contents.

As used herein, the term "bone" refers to the rigid organs that form part of the endoskeleton of vertebrates and function to move, support, and protect the various organs of the body, produce red and white blood cells and store minerals. One of the types of tissues that make up bone is the mineralized osseous tissue, also called bone tissue, which gives it rigidity and honeycomb-like three-dimensional internal structure. Other types of tissue found in bones include marrow, endosteum, and periosteum, nerves, blood vessels and cartilage.

Cartilage is a type of dense connective tissue composed of collagen fibers and/or elastin fibers that can supply smooth surfaces for the movement of articulating bones. Cartilage is found in many places in the body including the joints, the rib cage, the ear, the nose, the bronchial tubes and the intervertebral discs. There are three main types of cartilage: elastic, hyaline, and fibrocartilage.

Accordingly, the term "tissue" as used herein broadly encompasses all biological components including, but not limited to, skin, muscle, nerves, blood, bone, cartilage, teeth, tendons, ligaments, and organs composed of or containing same, as well as derivatives thereof, such as demineralized bone matrix. While the constructs and assemblies of the present invention have particular applicability to bone treatment, the present invention is not limited thereto. Rather, the teachings of the present invention may be applied to other analogous situations, in connection with other tissues and organs.

In the context of the present invention, the terms "plug", "plug material", "flowable plug" and "caulking" are used interchangeably to refer to any liquid, semi-solid, solid particulate or emulsion or gel material, or combinations thereof, which when implanted in tissue or the bore of a cannulated implant device, such as a bone screw, provides a full or partial hydraulic barrier to flow from one side of the plug along the linear axis of the hole or bore to the other side. Of particular value in the context of the present invention are viscous materials and materials which change viscosity or state after implantation. Typical materials are bio-compatible. Illustrative plug materials include, but are not limited to: bone cement, bone putty, mixtures of blood products and materials known to promote coagulation, bone and other waxes, thermoplastics, hydrogels, resins (including Methyl methacrylate (MMA)), foams, fats, demineralized bone matrix and the range of calcium based compounds known to those skilled in the art, autogenic and allogenic fluids, and combinations thereof. In the present invention, the use of solid particulates such as demineralized bone matrix to adjust the viscosity of the flowable plug allows a greater variety of otherwise low-viscosity liquids to be effectively used. This has particular utility in the case of a wax or thermoplastic material where the liquid state might be of insufficient viscosity and too readily flow out of the area before cooling and transitioning back to a solid state.

Additional components to imbue specific properties to the plug are also of value, such as, but not limited to the use of fibrin glue and related materials to increase the adhesion between the plug and the wall of the hole in the tissue or bore of the implant device. Bone void fillers, such as collagen mixed with calcium phosphate salt or other calcium molecule bearing compounds, or collagen mixed with demineralized bone matrix are readily available and are of value as plug materials in the context of the present invention. Of particular interest in the context of the present invention are materials and mixtures which expand through absorption of water or other materials, such as mixtures comprising, in part, hydrophilic materials which form hydrogels, or materials, such as sponge-like materials, which are maintained in a compressed state by a material with water soluble bonds are of particular interest. Plug materials which under go a state change through change in temperature, such as a bone wax which can transition from a liquid or semi-liquid state to a more solid state once implanted at body temperature are of value. Plug materials which undergo a reactive or solvent based transition to a more solid state are also of interest, such as epoxies, or other cements known to those skilled in the art.

In the context of the present invention, a flow barrier is anything that restricts or impedes, at least in part, the movement of material from one area to another. Typically this is a result of reduction in the open area available for the flow of material. Accordingly, plug materials can present either a complete barrier to flow, such as with a wax plug which occupies all the cross-sectional space, or a partial barrier to flow.

In the context of the present invention, in addition to serving as a proximal flow barrier, the plug of the present invention can also be used to itself deliver, either as a bolus or over an extended period of time, a therapeutic material which is identical to or separate from the therapeutic material which is injected; for example, there might be advantages to the plug containing anti-infectious agents. The therapeutic agents which may be contained (e.g., adsorbed) within and dispensed from, preferably over an extended period of time, the material of the plug are analogous to those which may be injected across the plug, via the hypodermic needle, and include those mentioned above. Specifically preferred examples include, but are not limited to, growth factors and other cytokines, stem and progenitor cells, antibiotics, chemotherapeutics and other cancer drugs, imaging compounds, analgesics, and the like as well as combinations thereof.

In the context of the present invention, the "therapeutics needle", "flow tube", hypodermic needle or other cannulated fluid delivery tube can comprise any fluid portal which can provide a hydraulic path between the proximal side of the plug and the distal side of the plug. The length and gauge of the needle required will vary with the length of the assembled device, the diameter of the hole being injected into and the propensity of the therapeutic material to plug. Of particular value in the context of the present invention is a hypodermic needle with a luer-lock-type fitting, such as might be found with a spinal needle; this type of needle typically has an extended length which makes it of value in transiting the length of the assembled device. In the context of the present invention, the therapeutics needle can be of any material which is compatible with being provided in a sterile state and does not adversely react with any other component in the system or the body tissue. Stainless steel is in common use for hypodermic needles and is well-suited to the device of the present invention. Polymer tubes, both rigid and flexible are also of value in the present invention. A collapsible tube which only passes fluid when sufficient pressure is introduced at one end is also of value in the present invention, and it should be noted that in such a case, the tube may not have to be removed from the plug after injection of the therapeutic material. The connection of the needle or tube to the therapeutic fluid reservoir and the fluid reservoir itself can be of any form readily envisioned by one skilled in the art; in the context of the present invention, a syringe with luer-lock-type connection is preferred because of the prevalence of these devices on the market.

The "plug pusher", "adapter section" and other body and protective sleeve sections of the present invention may be fabricated from any material having the requisite structural integrity to transit force applied by the surgeon to insert the plug into the hole or bore and maintain the plug in that position during injection of the therapeutic material. Typically, the proximal end (end away from the patient) of the assembled device will have some form of protuberance to afford the surgeon leverage in pushing the plug into the tissue and holding it there during injection and during the process of extracting the hypodermic needle. In the case of a luer-lock-type or other twist type connect on the needle, the plug pusher may, but is not required to, have a design which restricts the ability of the needle to rotate around the linear axis in relation to the plug pusher. Additionally, the plug pusher may, but is not required to, have a positive restraint to maintain the needle in the plug pusher until the surgeon wishes to remove it; said restraint can consist of a removable clip, or any other restraint as might be envisioned by one skilled in the art. Typically, the shaft of the plug pusher will have some type of indicia or mark(s) along the length of the shaft which are covered up by the plug guide cannula as the plug pusher is pushed into the plug guide to displace the plug into the tissue or implant device. The covering up of this mark (or marks) will provide the surgical personnel with a visible indication of the depth of insertion of the plug.

In the context of the present invention, in the assembled device the relative lengths between components 4, 2 and 1 in FIG. 1 and components 10, 8 and 1 in FIG. 3 provide a set linear relationship that determines and insures the relative position the needle discharge end, the forming plug and the depth of penetration in the target bone screw or tissue void.

The present invention is particularly useful for introducing therapeutic materials into the bore of a surgical implant, such as a bone screw. However, the invention is not limited to osteoimplants. It not only finds utility in connection with other type of implants or prosthetic devices but also finds utility in connection with bones or tissue alone, in the absence of such implants. Accordingly, the device and assembly of the present invention may used to introduce therapeutic materials into voids in tissue or bone through openings that are natural, disease-associated or surgically introduced. For example, the device and assembly of the present invention may used to deliver useful material to areas of necrotic or cancerous bone.

In addition to serving as a means for delivering therapeutic materials, the constructs of the present invention also find utility in the aspiration or removal of material from a hole or void in a tissue or bone, for example, aspirating bone marrow from the hip bone or aspirating excess fluid from an arthritic joint. The constructs of the present invention also have spinal column applications as well as potential utility in connection with soft organs and tissues.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to orthopedic bone screws, it is readily apparent that the present invention has other applications, such as those mentioned herein. As such, methods and materials similar or equivalent to those described herein can be used in the practice or testing of the present invention.

EXAMPLES

Example 1

Treatment of Chronic Degenerative Insertional Tendiopathy

Surgical treatment is provided for a patient with chronic degenerative insertional tendinopathy with thickening fibrosis and tearing of the Achilles tendon from the calcaneus extending approximately 5-6 cm, who has failed conservative treatment. In surgery, the peritinon is incised, the tendon is debrided and all non-viable tendon is removed, the diseased portion of the calcaneus is resected, and the flexor hallucis longus (FHL) tendon is approached. A 2 mmØ guide wire is driven into the calcaneus at the desired point of reattachment of the tendon. A 5 mmØ cannulated drill is then used over the guide wire to create the attachment tunnel. The free end of the portion of FHL tendon which remains attached to muscle is sutured and passed through the tunnel and appropriately tensioned before a 5.5 mmØ×3 mm PLA/PLGA interference screw is inserted in the tunnel to secure the tendon. The device of FIG. 3 is preloaded with a mixture of bone wax and demineralized bone matrix. The device is packaged within a sealed, sterile container and the package is heated in surgery to a temperature of 64° C. for twenty minutes prior to use. A syringe with 4 cc of autologous bone marrow aspirate concentrate is attached by means of a luer-lock fitting to the needle of the device of the present invention, and the syringe is depressed sufficiently to clear the needle of entrapped air. The device is then positioned at the head of the interference screw and the plug pusher and needle assembly is displaced such that the plug material is injected into the screw according to the method of the present invention. The bone was is permitted to harden for two minutes. The bone marrow aspirate is then injected into the region of the screw at the distal side of the plug. The needle is removed while the plug pusher is held in place, and then the plug pusher and plug guide assembly is removed.

Example 2

Treatment of Osteopenia and Interochanteric Femur Fracture

Surgical treatment is provided for a patient with an osteopenia and intertrochanteric femur fracture. The fracture is reduced and a hip screw and plate device is surgically inserted and affixed using 4.5 mmØ×4 cm cannulated titanium screws. In the process of screw placement, the screws are driven to a point representing 75% of the final insertion depth. At that point, a device of FIG. 1 is utilized in conjunction with the screw. A reservoir of methyl-methacrylate bone cement is attached as shown in FIG. 2 as component 7, to serve as the plug material The device is abutted to the partially inserted screw; the plug pusher is displaced into the plug guide cannula to a point where the plug and the needle tip are displaced into the target screw. The bone cement is then injected into the screw. A syringe comprising a media of allogenic Mesenchymal stem cells in autologous platelet rich plasma is attached as component 5 to the therapeutics needle and the contents are injected into the bone screw at the distal side of the plug. The needle is removed, and then the plug pusher is removed. The screw is then driven the remaining portion to full depth and, in this process, the driving bit provides the additional benefit of holding the plug in place in the screw during the process of driving the screw further into the bone.

INDUSTRIAL APPLICABILITY

The present invention provides a means for introducing and retaining a broad range of therapeutic cells, particularly stem cells, and other biologically significant and/or bioactive molecules in cannulated implants as well as in surgical holes in bone, cartilage, teeth and other tissue. Applicable procedures that would benefit from the devices and assemblies of the present invention are common in orthopedic surgery, including spinal surgery, and dentistry. The present invention provides the surgeon with tools and devices which are compatible with existing surgical techniques and permits a more focused delivery of often expensive therapeutic materials. The present invention has particular value in the introduction of stem and other precursor cells, bioactive cytokines, including but not limited to growth factors as well as to the introduction of anti-cancer drugs, particularly those having a toxic effect and for which restricted application is desired.

The devices, constructs, assemblies and methods presented herein provide for increased efficiency of operation in a surgical operating room environment with reduced potential for error. The devices, constructs, assemblies and methods also may result in fewer avenues of potential bacterial infections during surgeries. The efficiencies derived from the methods of the present invention can reduce the time in surgery, which, in turn, can reduce the stress on the patient's body and has the potential to reduce the cost of the surgical procedure. The ability to efficiently introduce and retain therapeutic materials may result in a faster recovery from a medical condition.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

What is claimed:

1. An assembly for delivering therapeutic material into a void in a tissue or implanted prosthetic device, said void accessed by means of a proximal opening, said assembly comprising:
   a. a flowable plug in a plug reservoir having a volume, a distal end and a proximal end and a linear axis extending therebetween;
   b. one or more fluid cannulated flow tubes, each having a distal and a proximal ends; wherein each of the proximal ends comprise an attachment point to a therapeutic fluid reservoir and each of the distal ends comprises a therapeutic fluid discharge point;
   c. a flowable plug delivery structure comprising:
      i. a plug reservoir cannula having a proximal end and a distal end and an axial bore extending therebetween, said bore comprising, in part, said flowable plug in said reservoir, and wherein said distal end comprises one or more flowable plug discharge ports serving as a path for discharging said flowable plug into said void;
      ii. a plug pusher that transmits a force to said plug reservoir housing said flowable plug so as to discharge said flowable plug through said one or more flowable plug discharge ports into said void; and
      iii. a mechanism that coordinates discharge of said flowable plug through said one or more flowable plug discharge ports with a distalward axial displacement of said one or more fluid cannulated flow tubes into said void.

2. The assembly of claim 1, wherein at least one of said one or more fluid cannulated flow tubes comprises a hypodermic needle.

3. The assembly of claim 1, wherein said flowable plug takes the form of a liquid, emulsion, suspension, foam, gel, or hydrogel and is fabricated from a material selected from the group consisting of a wax, fat, thermoset resin, thermoplastic, acrylate resin, blood products, and bone products.

4. The assembly of claim 3, wherein said flowable plug is comprised, at least in part, of a bone product selected from the group consisting of bone, bone cement, bone was, bone matrix, bone putty, bone gel and combinations thereof.

5. The assembly of claim 1, wherein said flowable plug comprises one or more components and said plug reservoir comprises one or more sections.

6. The assembly of claim 1, wherein the one or more therapeutic materials is selected from the group consisting of stem cells, progenitor cells, biological cells, BMP, PDGF, TGF, growth factors, antimicrobials, clotting agents, fibronectin, anticoagulants, platelet rich plasma, platelet poor plasma and adipose tissue.

7. The assembly of claim 1, wherein said plug pusher comprises an elongated shaft having a plunger component at its distal end.

8. The assembly of claim 1, wherein relative linear dimensions of the one or more fluid cannulated flow tubes, the plug reservoir cannula, the plug pusher and the flowable plug are such that when used together,
   a. the distal ends of said one or more fluid cannulated flow tubes are deployed at a predetermined depth into said tissue or implanted prosthetic device,
   b. the flowable plug is injected at a predetermined depth, and
   c. a relationship of the distal ends of said one or more fluid cannulated flow tubes and the distal end of the flowable plug is predetermined and allows for free passage of therapeutic material through said one or more fluid cannulated flow tubes to a distal side of the flowable plug in the target void.

9. The assembly of claim 1, wherein said therapeutic fluid reservoir contains stem cells, other biological cells or therapeutic molecules.

10. The assembly of claim 1, wherein said one or more fluid reservoirs contains material selected from the group consisting of bone marrow products, blood products, adipose tissue products, and fluids from the reproduction system or products thereof.

11. The assembly of claim 1, wherein said mechanism for coordinating simultaneous distalward axial displacement of said flowable plug and said one or more fluid cannulated flow tubes comprises a force transmitting contact or linkage between one of said fluid cannulated flow tubes and said plug pusher.

12. The assembly of claim 1, wherein said mechanism for coordinating simultaneous axial displacement of said flowable plug and said one or more fluid cannulated flow tubes comprises a linkage between one of said fluid cannulated flow tubes and said plug pusher.

13. The assembly of claim 12, wherein said linkage comprises a locked configuration, wherein said flow tube and plug pusher move as a single unit, and an unlocked configuration, wherein the plug pusher maintains the plug in position while said flow tube is retracted.

14. An assembly for delivering therapeutic material into a void in a tissue or implanted prosthetic device, said void accessed by means of a proximal opening, said assembly comprising:
   a. one or more flowable plug delivery cannulas;
   b. an assembly body having a proximal end and a distal end with a flowable plug discharge port at the distal end of said assembly body, wherein said discharge port is hydraulically connected to a flowable plug in a plug reservoir;
   c. one or more fluid cannulated flow tubes, each having a proximal end and a distal end, wherein each of the proximal ends comprises an attachment point to a therapeutic fluid reservoir and each of the distal ends comprises a therapeutic fluid discharge point and wherein said distal ends of said one or more of said fluid cannulated flow tubes are at a point more distal to the assembly body than said flowable plug discharge port;
   d. an adapter section at the distal end of said assembly body wherein said flowable plug discharge port and the distal ends of said one or more fluid cannulated flow tubes are located within a perimeter defining a surface wherein said surface is compatible with a medical implant or tissue void and provides at least a partial hydraulic seal with said void.

15. The assembly of claim 14, wherein relative linear dimensions of the one or more fluid cannulated flow tubes, the one or more flowable plug delivery cannulas, and the adapter section, the volume of said flowable plug and a dimension of the target void are such that when used together,
   a. the distal ends of the one or more fluid cannulated flow tubes are deployed at a predetermined depth into said tissue or implanted prosthetic device,
   b. the flowable plug is injected at a predetermined depth, and
   c. a relationship between the distal ends of the one or more fluid cannulated flow tubes and the distal end of the flowable plug is predetermined and allows for free passage of therapeutic material through said one or more fluid cannulated flow tubes to a distal side of the flowable plug in the target void.

16. A method for delivering therapeutic material into a void in a tissue or implanted prosthetic device, said void accessed by means of a proximal opening, using the assembly of claim 1, said method comprising the steps of:
   a. placing the one or more fluid cannulated flow tubes into contact with said plug pusher to form a unitary component;
   b. placing the distal end of the assembly in contact with said void, wherein said void comprises in part an opening in patient tissue;
   c. simultaneously displacing the distal ends of said fluid cannulated flow tubes into said void and said flowable plug; wherein the flowable plug is introduced at a point proximal to the distal end of said fluid tube in a manner to impede fluid outflow therethrough; and
   d. injecting one or more therapeutic materials through said one or more fluid cannulated flow tubes, into the void on a distal side of the plug material.

17. The method of claim 16, wherein said step (d) involves attaching a syringe or other reservoir containing one or more therapeutic materials to the proximal ends of said one or more fluid cannulated flow tubes.

18. The method of claim 16, wherein step (d) is followed by step (e): removing said one or more fluid cannulated flow tubes in a manner whereby the flowable plug and therapeutic material remain in the tissue or the implanted prosthetic device.

* * * * *